United States Patent
Tomasi (12)

(10) Patent No.: US 6,518,012 B1
(45) Date of Patent: Feb. 11, 2003

(54) METHOD FOR REGULATING THE EXPRESSION OF MHC ANTIGENS AND CD40 BY INHIBITORS OF HISTONE DEACETYLATION

(75) Inventor: Thomas B. Tomasi, Orchard Park, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 09/540,257

(22) Filed: Mar. 31, 2000

Related U.S. Application Data

(60) Provisional application No. 60/146,275, filed on Jul. 29, 1999, and provisional application No. 60/127,591, filed on Apr. 2, 1999.

(51) Int. Cl.$^7$ .............................. C12Q 1/00; C07H 5/04
(52) U.S. Cl. .......................................... 435/4; 536/18.7
(58) Field of Search .......................... 424/184.1, 278.1; 435/4; 536/18.7

(56) References Cited

U.S. PATENT DOCUMENTS

| | | | |
|---|---|---|---|
| 4,690,918 A | 9/1987 | Beppu et al. ............... 514/23 |
| 5,858,365 A | * 1/1999 | Faller | |
| 5,993,845 A | 11/1999 | Geerts et al. ............... 424/423 |

OTHER PUBLICATIONS

Glimcher et al, 1992, Ann. Rev. Immunol., 10:13.
Cabrera et al, 1995, Scand. J. Immunol., 41:398.
Chen et al, 1994, JEM, 179:523.
Siavoshian, S. et al. Butyrate modulates MHC class I and HLA–DR antigens expression on intestinal epithelial cells. Gastroenterology, 108: A917, 1995.*
Wadee, A.A. et al. HLA expression in hepatocellular carcinoma cell lines. Clin. Exp. Immunol., 97: 328–333, 1994.*
Komatsu, Y. et al. Histone deacetylase inhibitors up–regulate the expression of cell surface MHC class–I molecules in B16/BL6 cells. The Journal of Antibiotics, 51: 89–91, 1998.*
Saita, A. et al. A synthetic inhibitor of histone deacetylase, MS–27–275, with marked in vivo antitumor activity against human tumors. Proc. Natl. Acad. Sci. USA, 96: 4592–4597, 1999, Apr.*
Ogryzko et al. (Mol. Cell. Biol. vol. 9, 1996, pp. 5210–5218).*

* cited by examiner

*Primary Examiner*—Anthony C. Caputa
*Assistant Examiner*—Gary B. Nizkol
(74) *Attorney, Agent, or Firm*—Hodgson Russ LLP

(57) ABSTRACT

The present invention discloses compositions and methods for enhancing the expression of major histocompatability complex (MHC) and costimulatory antigens on tumor cells. The method comprises exposing the tumor cells to inhibitors of histone deacetylation.

3 Claims, 11 Drawing Sheets

Figure 5A
Figure 5C
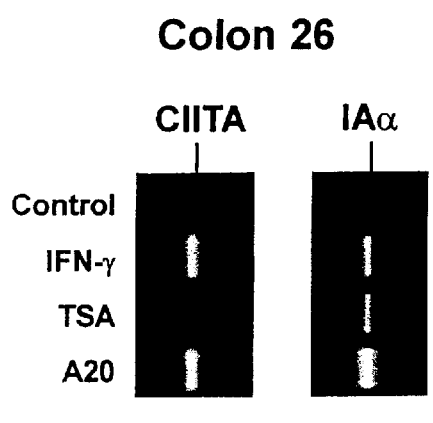
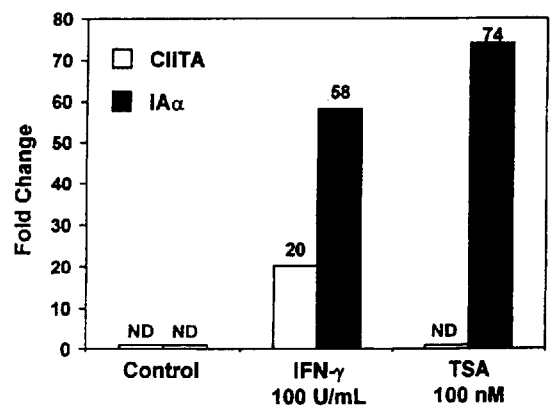
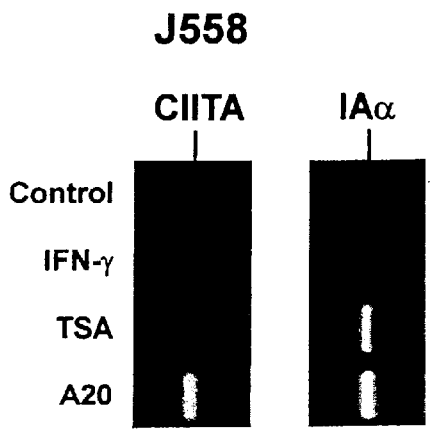
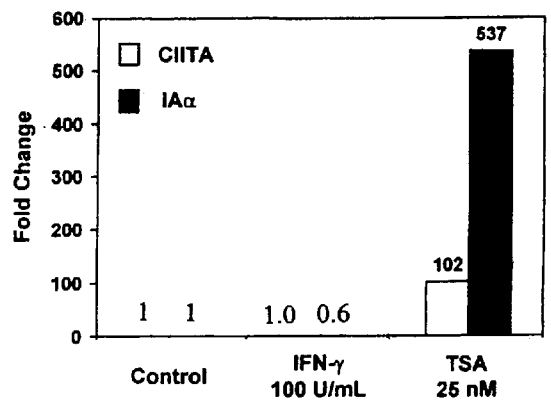
Figure 5B
Figure 5D

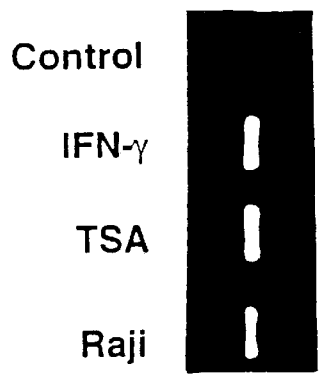 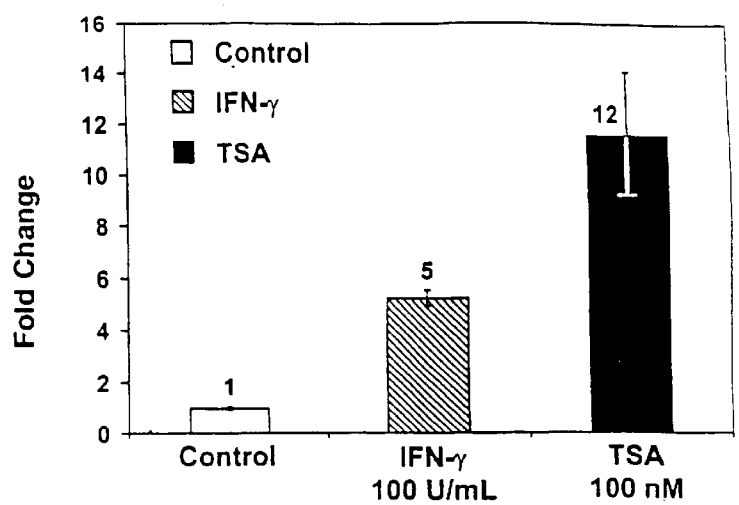
Figure 7A
Figure 7D

Primer and Probe Sequences Used for Real-time PCR

| Name | | Seq. Id. No. | Sequence (5'→3') | Amplicon Size (bp) |
|---|---|---|---|---|
| Human CIITA | Forward | 1 | AGCAGGCTGTTGTGTGACATG | 95 |
| | Reverse | 2 | TGGGAGTCCTGGAAGACATACTG | |
| | Probe | 3 | CCGCGATATTGGCATAAGCCTCCCT | |
| HLA-DRa | Forward | 4 | CTCTTCTCAAGCACTGGGAGTTT | 121 |
| | Reverse | 5 | ATGAAGATGGTCCCAATAATGATG | |
| | Probe | 6 | TGCTCCAAGCCCTCTCCCAGAGAC | |
| Human GAPDH | Forward | 7 | GAAGGTGAAGGTCGGAGTC | 226 |
| | Reverse | 8 | GAAGATGGTGATGGGATTTC | |
| | Probe | 9 | CAAGCTTCCCGTTCTCAGCC | |
| Human CD40 | Forward | 10 | CACCTCGCCATGGTTCGT | 150 |
| | Reverse | 11 | CAGTTCTGTCCTGGCTGGC | |
| | Probe | 12 | TGCCTCTGCAGTGCGTCCTCTGG | |
| Mouse CIITA | Forward | 13 | CAGATACCATCAACTGCGACCA | 169 |
| | Reverse | 14 | TCTGCTCCAATGTGCTCTATGAAG | |
| | Probe | 15 | TCGAGCTGGGTATCCTGGAACACGTACTG | |
| Mouse IAa | Forward | 16 | GCCTCTGCGGAGGTGAAGA | 134 |
| | Reverse | 17 | CAAGTCCACATAGAACAACTCATCACC | |
| | Probe | 18 | CGACATTGAGGCCGACCACGTAGG | |
| Mouse GAPDH | Forward | 19 | TGCACCACCAACTGCTTAG | 177 |
| | Reverse | 20 | GGATGCAGGGATGATGTTC | |
| | Probe | 21 | CAGAAGACTGTGGATGGCCCCTC | |
| Mouse CD40 | Forward | 22 | CCCTGCATGGTGTCTTTGC | 149 |
| | Reverse | 23 | GTCAGTCGGCTTCCTGGC | |
| | Probe | 24 | CGGCTGTGCGCGCTATGGG | |

Figure 9

SEQUENCE LISTING

<160> NUMBER OF SEQ ID NOS: 26

<210> SEQ ID NO 1
<211> LENGTH: 21
<212> TYPE: DNA

```
<213> ORGANISM: Artificial Sequence
<220> FEATURE:
<223> OTHER INFORMATION: Forward primer for Human CIITA

<400> SEQUENCE: 1
agcaggctgt tgtgtgacat g                                              21

<210> SEQ ID NO 2
<211> LENGTH: 23
<212> TYPE: DNA
<213> ORGANISM: Artificial Sequence
<220> FEATURE:
<223> OTHER INFORMATION: Reverse primer for Human CIITA

<400> SEQUENCE: 2
tgggagtcct ggaagacata ctg                                            23

<210> SEQ ID NO 3
<211> LENGTH: 25
<212> TYPE: DNA
<213> ORGANISM: Artificial Sequence
<220> FEATURE:
<223> OTHER INFORMATION: Probe primer for Human CIITA

<400> SEQUENCE: 3
ccgcgatatt ggcataagcc tccct                                          25

<210> SEQ ID NO 4
<211> LENGTH: 23
<212> TYPE: DNA
<213> ORGANISM: Artificial Sequence
<220> FEATURE:
<223> OTHER INFORMATION: Forward primer for HLA-DR

<400> SEQUENCE: 4
ctcttctcaa gcactgggag ttt                                            23

<210> SEQ ID NO 5
<211> LENGTH: 24
<212> TYPE: DNA
<213> ORGANISM: Artificial Sequence
<220> FEATURE:
<223> OTHER INFORMATION: Reverse primer for HLA-DR

<400> SEQUENCE: 5
atgaagatgg tcccaataat gatg                                           24

<210> SEQ ID NO 6
<211> LENGTH: 24
<212> TYPE: DNA
<213> ORGANISM: Artificial Sequence
<220> FEATURE:
<223> OTHER INFORMATION: Probe primer for HLA-DR

<400> SEQUENCE: 6
tgctccaagc cctctcccag agac                                           24

<210> SEQ ID NO 7
<211> LENGTH: 19
<212> TYPE: DNA
<213> ORGANISM: Artificial Sequence
<220> FEATURE:
<223> OTHER INFORMATION: Forward primer for Human GAPDH

<400> SEQUENCE: 7
gaaggtgaag gtcggagtc                                                 19
```

```
<210> SEQ ID NO 8
<211> LENGTH: 20
<212> TYPE: DNA
<213> ORGANISM: Artificial Sequence
<220> FEATURE:
<223> OTHER INFORMATION: Reverse primer for Human GAPDH

<400> SEQUENCE: 8
gaagatggtg atgggatttc                                                20

<210> SEQ ID NO 9
<211> LENGTH: 20
<212> TYPE: DNA
<213> ORGANISM: Artificial Sequence
<220> FEATURE:
<223> OTHER INFORMATION: Probe primer for Human GAPDH

<400> SEQUENCE: 9
caagcttccc gttctcagcc                                                20

<210> SEQ ID NO 10
<211> LENGTH: 18
<212> TYPE: DNA
<213> ORGANISM: Artificial Sequence
<220> FEATURE:
<223> OTHER INFORMATION: Forward primer for Human CD40

<400> SEQUENCE: 10
cacctcgcca tggttcgt                                                  18

<210> SEQ ID NO 11
<211> LENGTH: 19
<212> TYPE: DNA
<213> ORGANISM: Artificial Sequence
<220> FEATURE:
<223> OTHER INFORMATION: Reverse primer for Human CD40

<400> SEQUENCE: 11
cagttctgtc ctggctggc                                                 19

<210> SEQ ID NO 12
<211> LENGTH: 23
<212> TYPE: DNA
<213> ORGANISM: Artificial Sequence
<220> FEATURE:
<223> OTHER INFORMATION: Probe primer for Human CD40

<400> SEQUENCE: 12
tgcctctgca gtgcgtcctc tgg                                            23

<210> SEQ ID NO 13
<211> LENGTH: 22
<212> TYPE: DNA
<213> ORGANISM: Artificial Sequence
<220> FEATURE:
<223> OTHER INFORMATION: Forward primer for Mouse CIITA

<400> SEQUENCE: 13
cagataccat caactgcgac ca                                             22

<210> SEQ ID NO 14
<211> LENGTH: 24
<212> TYPE: DNA
<213> ORGANISM: Artificial Sequence
<220> FEATURE:
```

```
<223> OTHER INFORMATION: Reverse primer for Mouse CIITA

<400> SEQUENCE: 14
tctgctccaa tgtgctctat gaag                                          24

<210> SEQ ID NO 15
<211> LENGTH: 29
<212> TYPE: DNA
<213> ORGANISM: Artificial Sequence
<220> FEATURE:
<223> OTHER INFORMATION: Probe primer for Mouse CIITA

<400> SEQUENCE: 15
tcgagctggg tatcctggaa cacgtactg                                     29

<210> SEQ ID NO 16
<211> LENGTH: 19
<212> TYPE: DNA
<213> ORGANISM: Artificial Sequence
<220> FEATURE:
<223> OTHER INFORMATION: Forward primer for Mouse IA

<400> SEQUENCE: 16
gcctctgcgg aggtgaaga                                                19

<210> SEQ ID NO 17
<211> LENGTH: 27
<212> TYPE: DNA
<213> ORGANISM: Artificial Sequence
<220> FEATURE:
<223> OTHER INFORMATION: Reverse primer for Mouse IA

<400> SEQUENCE: 17
caagtccaca tagaacaact catcacc                                       27

<210> SEQ ID NO 18
<211> LENGTH: 24
<212> TYPE: DNA
<213> ORGANISM: Artificial Sequence
<220> FEATURE:
<223> OTHER INFORMATION: Probe primer for Mouse IA

<400> SEQUENCE: 18
cgacattgag gccgaccacg tagg                                          24

<210> SEQ ID NO 19
<211> LENGTH: 19
<212> TYPE: DNA
<213> ORGANISM: Artificial Sequence
<220> FEATURE:
<223> OTHER INFORMATION: Forward primer for Mouse GAPDH

<400> SEQUENCE: 19
tgcaccacca actgcttag                                                19

<210> SEQ ID NO 20
<211> LENGTH: 19
<212> TYPE: DNA
<213> ORGANISM: Artificial Sequence
<220> FEATURE:
<223> OTHER INFORMATION: Reverse primer for Mouse GAPDH

<400> SEQUENCE: 20
ggatgcaggg atgatgttc                                                19
```

```
<210> SEQ ID NO 21
<211> LENGTH: 23
<212> TYPE: DNA
<213> ORGANISM: Artificial Sequence
<220> FEATURE:
<223> OTHER INFORMATION: Probe primer for Mouse GAPDH

<400> SEQUENCE: 21
cagaagactg tggatggccc ctc                                         23

<210> SEQ ID NO 22
<211> LENGTH: 19
<212> TYPE: DNA
<213> ORGANISM: Artificial Sequence
<220> FEATURE:
<223> OTHER INFORMATION: Forward primer for Mouse CD40

<400> SEQUENCE: 22
ccctgcatgg tgtctttgc                                              19

<210> SEQ ID NO 23
<211> LENGTH: 18
<212> TYPE: DNA
<213> ORGANISM: Artificial Sequence
<220> FEATURE:
<223> OTHER INFORMATION: Reverse primer for Mouse CD40

<400> SEQUENCE: 23
gtcagtcggc ttcctggc                                               18

<210> SEQ ID NO 24
<211> LENGTH: 19
<212> TYPE: DNA
<213> ORGANISM: Artificial Sequence
<220> FEATURE:
<223> OTHER INFORMATION: Probe primer for Mouse CD40

<400> SEQUENCE: 24
cggctgtgcg cgctatggg                                              19

<210> SEQ ID NO 25
<211> LENGTH: 20
<212> TYPE: DNA
<213> ORGANISM: Artificial Sequence
<220> FEATURE:
<223> OTHER INFORMATION: Forward primer for Mouse CIITA

<400> SEQUENCE: 25
acacctggac ctggactcac                                             20

<210> SEQ ID NO 26
<211> LENGTH: 20
<212> TYPE: DNA
<213> ORGANISM: Artificial Sequence
<220> FEATURE:
<223> OTHER INFORMATION: Reverse primer for Mouse CIITA

<400> SEQUENCE: 26
gctcttggct cctttgtcac                                             20
```

METHOD FOR REGULATING THE EXPRESSION OF MHC ANTIGENS AND CD40 BY INHIBITORS OF HISTONE DEACETYLATION

This application claims the priority of U.S. Provisional Application No. 60/127,591 filed on Apr. 2, 1999, and No. 60/146,275 filed on Jul. 29, 1999, the disclosures of which are incorporated herein by reference.

FIELD OF INVENTION

This invention relates to the field of tumor immunogenicity. More particularly, this invention, provides a method for increasing the expression of MHC class I and class II antigens, and costimulatory molecules by administration of inhibitors of histone deacetylation.

BACKGROUND OF THE INVENTION

It is generally considered that tumorogenesis is related, in part, to failure of the immune system to reject spontaneously arising tumors by responding appropriately to tumor antigens. In a normal immune response, induction of T-lymphocytes is considered to be a critical initial step. Activation of T cells results in T cell proliferation, cytokine production by T cells and generation of T cell mediated effector functions. T cell activation requires an antigen-specific signal, which involves the participation of the antigenic peptide as well as major histocompatability complex (MHC) class I or class II proteins.

MHC class II molecules function primarily to present peptides derived from exogenous antigens to CD4 helper T cells. Effective presentation and activation of T cells requires a second signal delivered by costimulation molecules (Allison et al., 1995, Curr. Opin. Immunol. 7:682). The constitutive expression of MHC class II molecules is restricted to a few cell types, the antigen presenting cells (APCS) which include B lymphocytes, dendritic cells and some macrophages. However, many normal cells including epithelial cells, endothelial cells, astrocytes, resting T cells and some monocytes/macrophages express MHC class II after activation by various stimuli especially gamma-interferon (IFNγ; see Glimcher et al., 1992, Ann. Rev. Immunol., 10:13). Only a few cell types, including mature oligodendrocytes, sensory neurons, trophoblasts, and some tumor cells cannot be induced to express class II by IFNγ.

While a few tumor cells display nearly normal levels of cell surface MHC class II, most do not (Cabrera et al., 1995, J. Immunol., 41:398). In some class II negative tumor cells, the class II transactivator (CIITA) is non-inducible and these cells fail to transcribe mRNA for class II after treatment with IFNγ but will, if transfected with CIITA. Also, genes encoding costimulatory molecules which are required for activation of T cells are not expressed by many tumor cells (Chen et al., 1994, JEM, 179:523). Although these data suggest that the expression of MHC genes and costimulatory molecules is altered in some tumors, it is not clear how their expression relates to tumor immunogenicity. Thus, there continues to be need to identify factors and methods by which tumor immunogenicity can be increased so as to make tumors more amenable to immunotherapy.

SUMMARY OF THE INVENTION

The present invention discloses a method for enhancing the cell surface expression of MHC antigens on tumor cells. It was observed that low concentrations of deacetylase inhibitors (DAIs) that produced little or no apoptosis, and maintain an essentially normal cell cycle, induced the expression of MHC class I and class II, and CD40.

Thus, an object of the present invention is to provide a method for increasing the immunogenicity of tumors by inhibitors of deacetylation.

Another object of the present invention is to induce the expression of MHC genes and other molecules of immuno-logic importance in antigen presentation and cell lysis on cells, by exposure to inhibitors of histone deacetylation.

BRIEF DESCRIPTION OF THE FIGURES

FIGS. 5A–D are representations of the effect of IFNγ and the deacetylase inhibitor TSA on mRNA levels of CIITA and IAα in mouse tumor models J558 and Colon 26.

FIGS. 7A–F are representations of the effect of IFNγ and the deacetylase inhibitor TSA on mRNA levels of CD40 in human neuroblastoma cells SK-N-MC (A,D), and mouse tumor models Colon 26 (B,E) and J558 (C,F).

FIG. 9 is a representation of the primer and probe sequences used for real-time PCR.

DETAILED DESCRIPTION OF THE INVENTION

Figure 1:
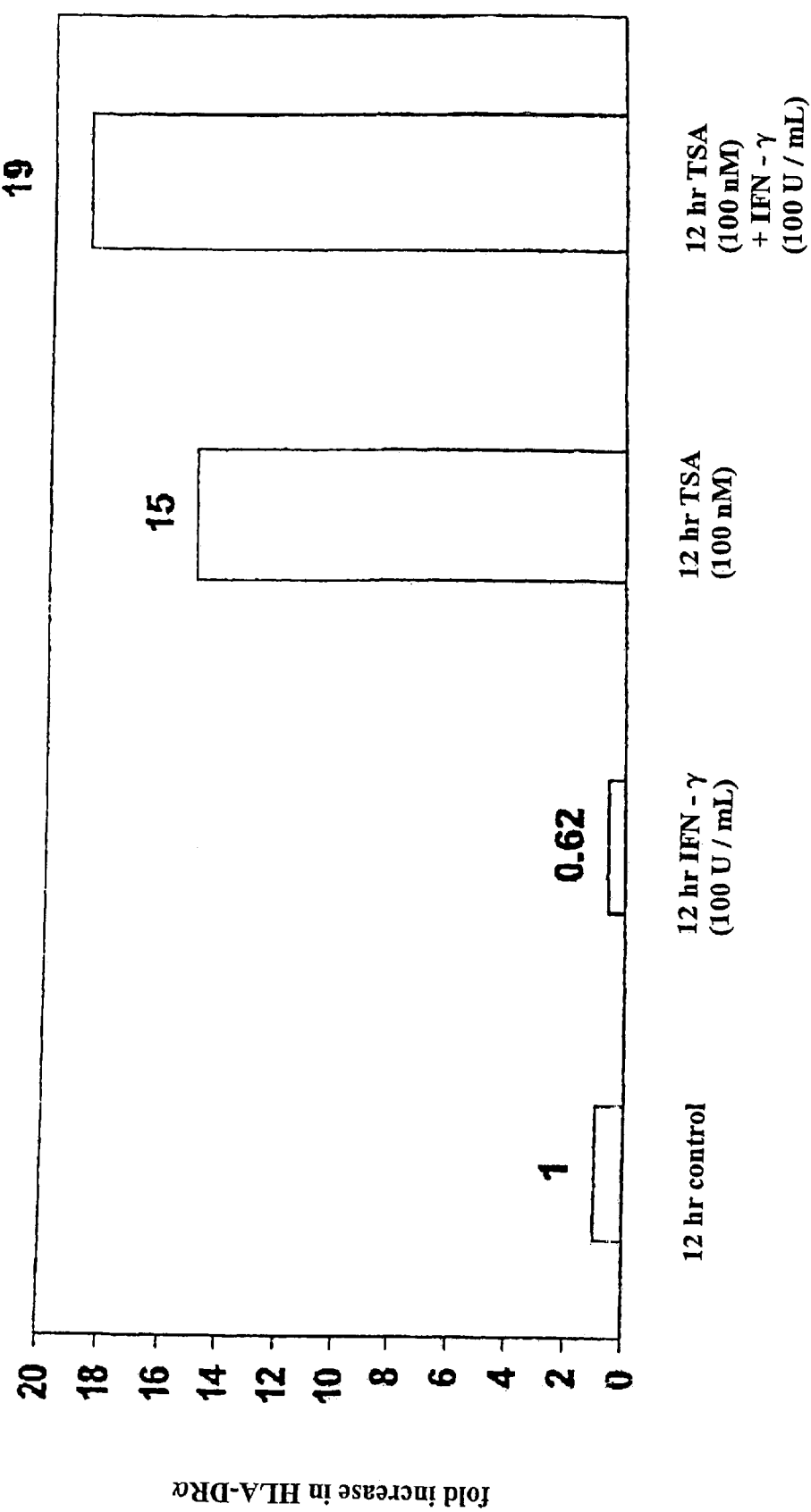
FIG. 1 is a representation of the effect of IFNγ and the deacetylase inhibitor TSA on the HLA-DRα mRNA in human trophoblast JAR cells.

This invention is directed to increasing the immunogenicity of tumors and their susceptibility to lysis by enhancing the expression of MHC class II and class I gene expression as well as the expression of costimulatory molecules such as CD40. The method of the present invention comprises administering to an individual, an effective dose of a deacetylase inhibitor, or exposing an excised tumor in vitro to the deacetylase inhibitors (DAIs).

For increasing the immunogenicity of tumor cells and for obtaining vaccines against tumors, inhibitors of histone deacetylation could potentially be applied in vivo or in vitro. For example, tumor cells can be excised and exposed to the inhibitors and subsequently used for the generation of an immune response. Alternatively, the inhibitors, can be delivered to the tumor cells in a pharmaceutically acceptable carrier by conventional routes known to those skilled in the art. For example, a DAI may be delivered by oral, intravenous, intraperitoneal, subcutaneous or intramuscular route. Further, DAIs may be delivered either through the blood stream or directly to the tumor site by methods known to those skilled in the art (see for example U.S. Pat. No. 5,993,845, incorporated herein by reference). Such methods include direct deposition at the tumor site or specific targeting of tumor cells (such as via conjugation with antibodies to tumor cell specific or tumor vasculature specific antigens).

The deacetylase Inhibitors (DAIs) of the present invention cause an inhibition of the activity of histone deacetylase. These compounds include, but are not limited to, trichostatin A, B and C, sodium butyrate, trapoxin, apicidin A, HC toxin and dupedecin. These compounds also include hybrid polar histone deacetylase inhibitors.

The dosage for a particular individual will vary according to the delivery route and other considerations such as weight, sex, age, and stage of disease. The appropriate dosage can be determined empirically by means well within the purview of those skilled in the art. For evaluating the response to the DAI, biopsies may be performed to monitor the expression of MHC genes or CD40 by standard means, such as those described herein. A daily dosage of 0.05 to 100 mg for an adult has been used for anti-fibrotic (U.S. Pat. No. 5,993,845) and anti-tumor (U.S. Pat. No. 4,690,918) uses and can be used as a starting point for the present invention. When tumors are excised and treated in vitro with the deacetylase inhibitors, the expression of MHC genes and CD40 can be monitored by standard means such as those described herein.

Formulations for administration of DAIs of the present invention include soft and hard capusules, tablets, granules, powders and the like for oral administration, and injection or drip infusion formulations for intravenous, intramuscular, subcutaneous routes, and other various solid, liquid or suspension formulations for targeted delivery. The amount of the active ingredients in the pharmaceutical composition may vary but is usually from 0.1% to about 50% by weight.

The present invention is described below in further detail by providing examples using human cells lines and animal tumor models. These examples are for illustrative purposes only and are not intended to be restrictive.

The source of various cell lines and other materials used in the examples provided herein is as follows. Human trophoblast cell line JAR and the neuroblastoma tumor cell line SK-N-MC were obtained from ATCC and shown to be free of mycoplasm by PCR testing. Cells were cultured in RPMI 1640 supplemented with 10% FCS, 1 mM Hepes, 10 mM sodium pyruvate. The mouse plasmacytoma J558, and mouse mastocytoma P815 were also obtained from ATCC. Stock and working dilutions of TSA were prepared according to package insert instructions using ethanol as diluent. Phycoerythrin-conjugated antibodies to murine surface markers H-2D$^d$ (clone 34-2-12), I-A$^d$ (AMS-32.1), CD40 (3/23) were purchased from Pharmingen (San Diego, Calif.). Flow cytometry reagents for human cells PE-anti HLA-A, B, C clone G46-2.6 was purchased from Pharmingen (San Diego, Calif.), PE-anti HLA-DR clone 243 from Becton Dickinson (San Jose, Calif.) and PE-anti CD40 clone mAb89 from Immunotech/Coulter (Marseilles, France).

EXAMPLE 1

This embodiment demonstrates that deacetylase inhibitors induce MHC class II genes. Two representative DAIs, TSA and NaBu were used for this illustration. First, toxicity at various concentrations of these inhibitors was determined by using four techniques: 1) for adherent cells 'lift-off' from tissue culture plates; 2) trypan-blue dye exclusion; 3) apoptosis as measured by a laddering technique performed as previously described (Robinson et al, 1997, *Biochemistry* 36:11169–11178), and flow cytometric analysis with propidium iodide (PI) or annexin-V. Concentrations of TSA from 5 nM to 250 nM for 6 to 72 hr and 1 mM Na-butyrate for 12–48 hr were found to be non toxic for the cell lines employed. In some experiments, 100 U/ml γ-IFN was added with and without the deacetylase inhibitor.

To determine the effect of DAIs on HLA-DRα mRNA, cytoplasmic RNA was isolated from untreated and treated human trophoblast cell line JAR using standard techniques (RNeasy System from Qiagen). Standard PCR was performed using primers for DR and CIITA (Murphy et al., 1998, Reprod Dev., Chin et al., 1994, Immunity 1:687–697). Other primers used included human and mouse GAPDH (Clontech) and forward primer 5'-ACACCTGGACCTGGACTCAC-3' (SEQ ID NO:25) and reverse primer 5'-GCTCTTGGCTCCTTTGTCAC-3' (SEQ ID NO:26) for mouse CIITA. PCR products were amplified with GOLD Taq for 10 min at 95° C., then 95° C. for 30 sec, 60° C. for 60 sec (25–45 cycles), then an extension at 60° C. for 10 min.

At high cycle PCR (40–45 cycles) with GOLD Taq polymerase, the human trophoblast cell line JAR showed a weak expression of mRNA for HLA-DRα. Treatment of JAR with 100 nM or with 250 nM TSA or 1 mM of sodium butyrate, resulted in a substantial increase in the levels of mRNA for DR while CIITA transcription remained undetectable at 35 cycles.

In order to obtain more quantitative information on fold changes in DR and CIITA after treatment with the deacetylase inhibitors, a real time fluorescence technique capable of quantitating low copy numbers of transcripts was carried out as follows. Oligonucleotide primers and TaqMan 5'-6-FAM and 3'-TAMRA-labeled probes were synthesized in the RPCI Biopolymer Facility. Primer and probe sequences are listed under Sequence Listing and also in FIG. 9. Sequences were designed using standard software (PrimerExpress software, PE Biosystems) except for human GAPDH.

Realtime PCR reactions contained TaqMan Universal PCR Master Mix (PE Biosystems), primers at 300 nM, and probes at optimal concentrations (150–225 nM depending on gene). Reactions were carried out on an ABI PRISM 7700 Sequence Detection System (PE Biosystems). Cycling conditions were 50° C. for 2 min, 95° C. for 10 min, then 60 cycles of 95° C. for 15 sec, 60° C. for 1 min. PCR samples were run in triplicate. The detection system and quantitative PCR was carried out as described by Williamson et al. (1995, *Genet Res.* 65:83–93). The threshold cycle number $C_T$ corresponded to the cycle number, at which the fluorescent emission reaches 10 standard deviations above the mean fluorescent emission, measured during the early 'baseline' cycles of the PCR. The $C_T$ values for triplicates were averaged and normalized to GAPDH levels. If two or more of the three replicates did not amplify after 40 cycles, the gene for that sample was considered nondetectable (ND). In such cases, in order to calculate a minimum fold change for other samples in the same group, the $C_T$ value was arbitrarily set at 40. Validation experiments showed a linear relationship between input cDNA and $C_T$ values over a range of serial dilutions of cDNA extending from 1 to $10^{-6}$ indicating that PCR efficiencies for each of the primer sets were close to 100%. Assuming reverse transcription efficiencies were approximately the same for each sample, relative amounts of mRNA using the comparative $C_T$ method. Fold changes in mRNA levels were calculated as $2^x$ where x=the difference between normalized $C_T$ values of the control and experimental samples.

Figure 2:
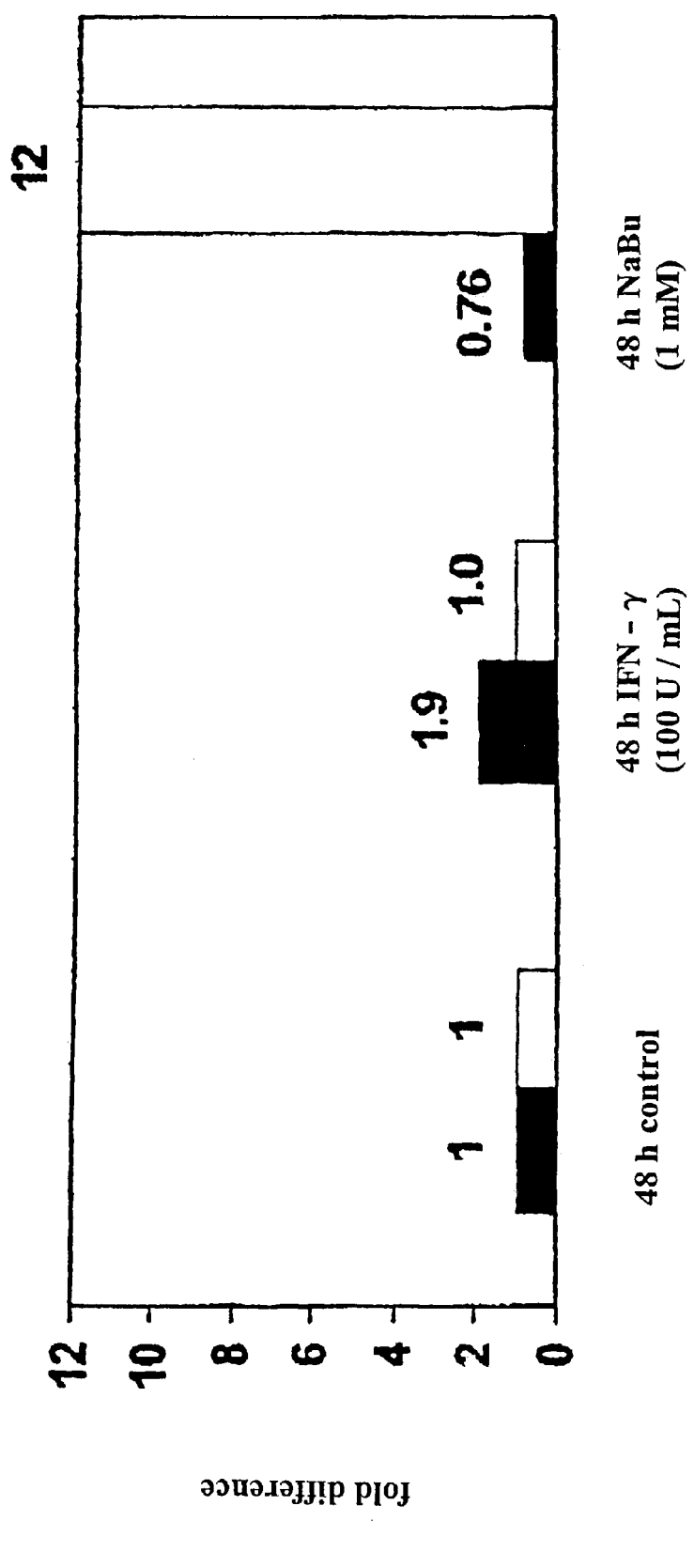
FIG. 2 is a representation of the effect of sodium butyrate on HLA-DRα mRNA and CIITA in human trophoblast JAR cells.

To evaluate the effects of DAIs on human cells, the human trophoblast cell line was treated with 100 nM Trichostatin A (TSA), IFNγ (100 U/ml) or a combination of TSA and IFNγ for 12 hours. RNA was isolated and real time quantitative RT-PCR was carried out. The fold increase in mRNA over the control was calculated. As shown in FIG. 1, JAR cells do not constitutively express, and cannot be induced to express MHC class II by IFNγ. However, TSA or TSA plus IFNγ produced a 15 fold and 19 fold increase in gene expression, respectively. The histone deacetylatase inhibitor, sodium butyrate also induced an increase in MHC class II mRNA. As shown in FIG. 2, sodium butyrate induced a 12 fold increase in mRNA for HLA-DRα in JAR cells compared to the control, and no increase in the class II transactivator (CIITA) was observed. IFNγ alone did not induce MHC class II gene expression.

Figure 3B:
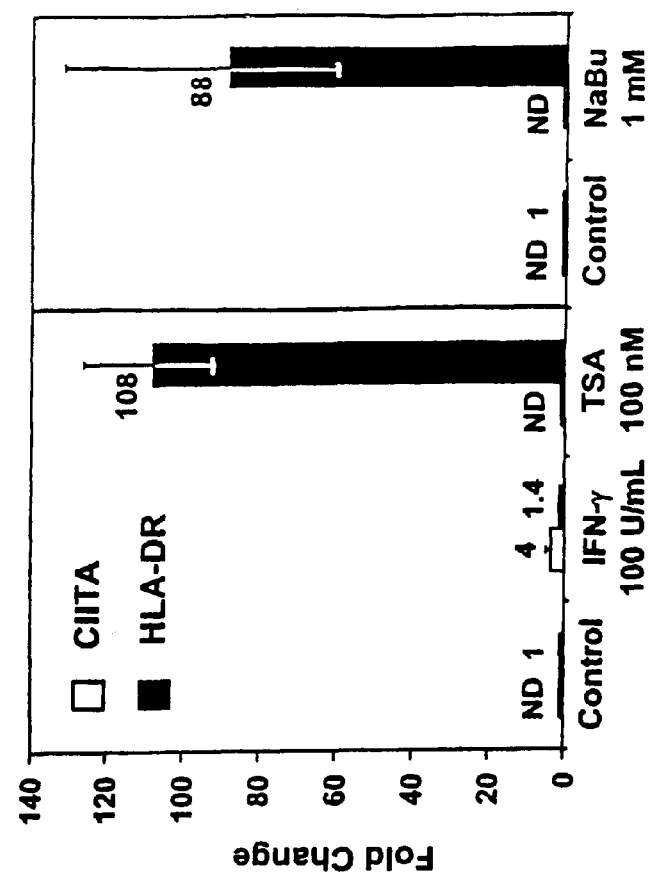
FIGS. 3A and 3B are representations of the effect of IFNγ and deacetylase inhibitors TSA and sodium butyrate on HLA-DRα mRNA in the human neuroblastoma cell line SK-N-MC.
Figure 3A:
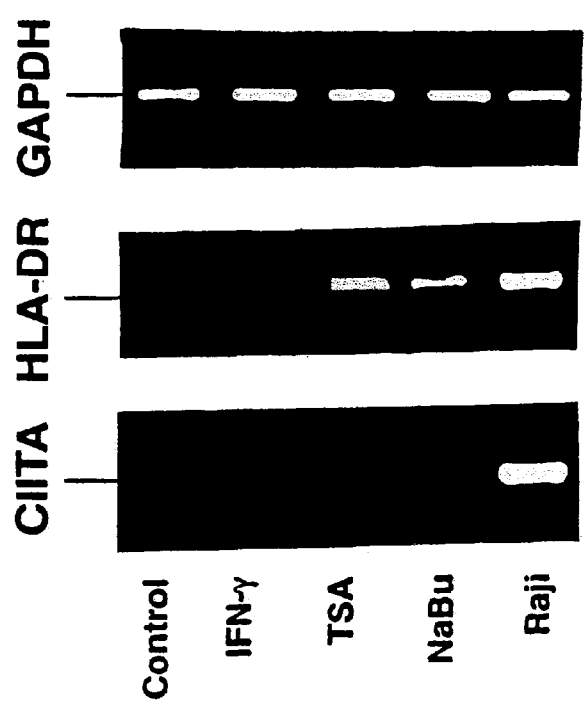

A similar effect of TSA and sodium butyrate was seen in the human neuroblastoma cell line SK-N-MC. As shown in FIG. 3A, treatment of the SK-N-MC cells with 100 nM TSA or 1 mM NaBu at the time of maximal expression (24 hours for TSA and 48 hours for NaBu) resulted in a substantial increase in the levels of mRNA for HLA-DRα (DR) as measured by RT-PCR, while CIITA transcription remained undetectable. Levels of mRNA for the housekeeping gene, GAPDH, remained unchanged after treatment (FIG. 3B). mRNA for the DP and DQ isotypes of MHC class II were also induced by TSA (data not shown). Whereas TSA and NaBu activate transcription of MHC class II in MC tumor cells, these cells cannot be induced to express mRNA for DR by IFNγ (FIG. 3A). This is not due to the failure of MC cells to express IFNγ receptors or to a defect in the IFNγ signaling pathway, since mRNA for two prototype IFNγ inducible genes, interferon regulatory factor (IRF-1) and guanylate binding protein (GBP), is enhanced by IFNγ treatment and MC has IFNγ receptors measurable by flow cytometry (data not shown).

In order to obtain more quantitative information on gene expression after treatment with DAIs, real time fluorescent PCR technique capable of detecting low levels of mRNA, was carried out as described above, and fold changes in transcript level using $C_T$ values standardized to GAPDH were calculated. As shown in FIG. 3B, treatment of MC cells with 100 nM TSA for 24 hr resulted in a 108-fold increase in expression of DR, but no increase in CIITA was detectable even after 60 cycles of PCR. NaBu treatment (1 mM, 48 hr) resulted in an 88-fold enhancement in DR but no activation of CIITA (FIG. 3B). Thus, within the limits of these quantitative measurements, the activation of DR gene expression by DAIs appears to occur with no change in the level of CIITA transcripts. Although IFNγ did not stimulate DR at any concentration or time point studied, this cytokine did elicit low levels of CIITA mRNA detectable by real time (4-fold) (FIG. 3B), that were not detected by routine PCR at 35 cycles (FIG. 3A).

EXAMPLE 2

Figure 4:
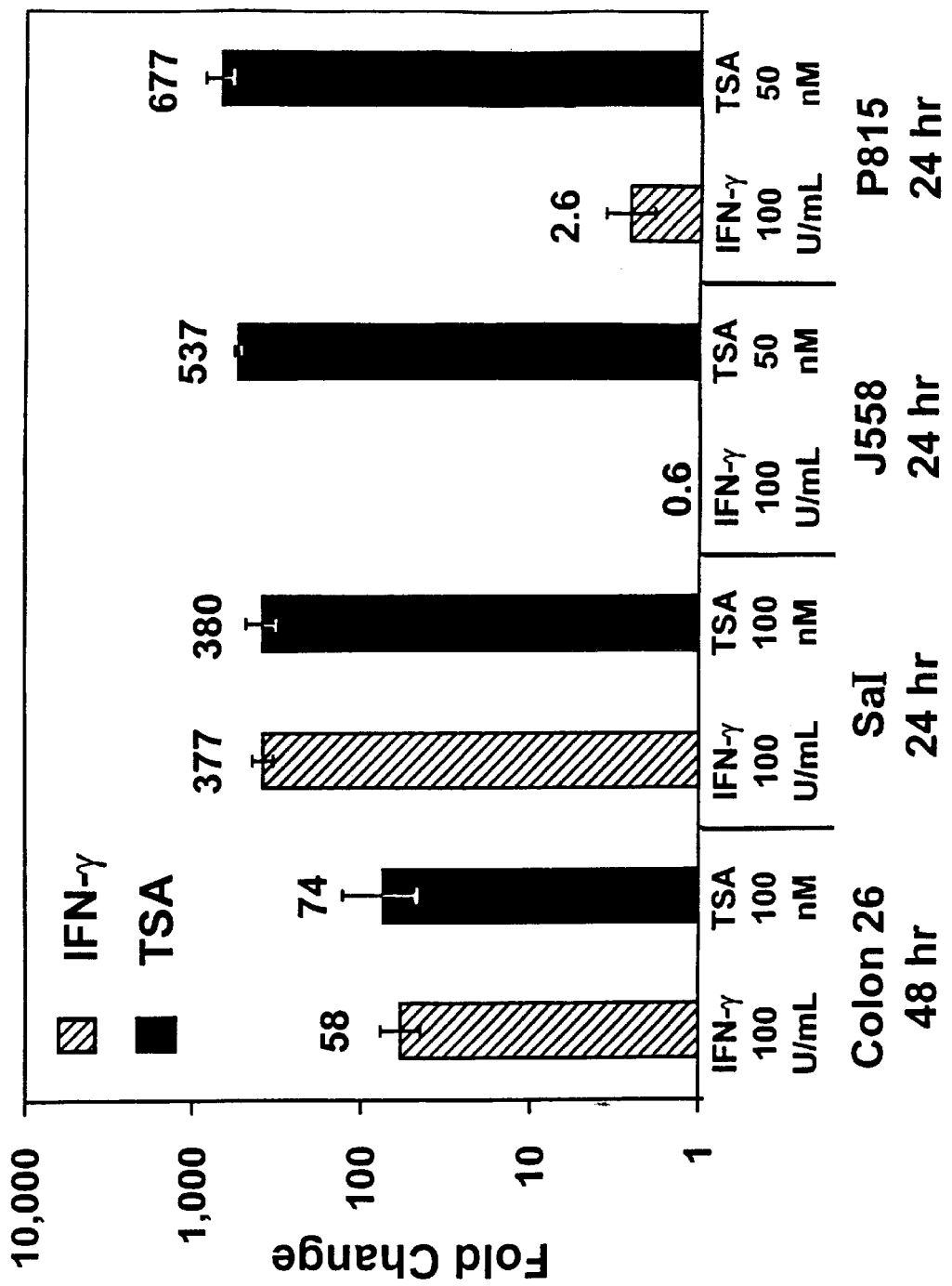
FIG. 4 is a representation of the effect of IFNγ and the deacetylase inhibitors TSA on mRNA levels of IAα in mouse tumor models, Colon 26, SaI, J558 and P815.

This embodiment demonstrates that DAIs increase MHC class II gene expression in animal tumor models. To determine if the effect of DAIs on MHC class II was manifested in other tumors and in different species, the effect of TSA was tested on four commonly used mouse tumor models: the SaI fibrosarcoma, the Colon 26 adenocarcinoma, the J558 plasmacytoma and the P815 mastocytoma. TSA induced class II in all four mouse tumors examined, while the effects of IFNγ were variable (FIG. 4). Data presented for each cell line represents optimal incubation time and concentration of TSA and is compared with 100 U/ml of IFNγ at the same time point. Numbers over bars represents fold changes. IFNγ activated nearly equivalent fold-increases in class II as did TSA in both SaI and Colon 26, but failed to induce class II in J558 and only weakly enhanced P815 class II mRNA. Colon 26 and J558 that differed strikingly in their reactivity to IFNγ were selected for further evaluation. RT-PCR and real time PCR was used to examine induction of CIITA and IAα by TSA and IFNγ. A20, a constitutively positive B cell line was used as a positive control. The results are shown in FIGS. 5A–D. The numbers over bars represent fold changes. Analysis by standard RT-PCR at 35 cycles, showed that IFNγ induced expression of CIITA and class II in Colon 26 and, similar to the human MC cell line, CIITA was not detected after TSA treatment (FIG. 5A). Real-time PCR analysis of Colon 26 cells (FIG. 5C) was consistent with the RT-PCR data and demonstrated that TSA induced a 74-fold increase in Ia in the absence of CIITA while IFNγ elicited both CIITA (20-fold) and Iα (58-fold) expression. The J558 cell line behaved quite differently from Colon 26 in that IFNγ did not activate either CIITA or class II (FIG. 5B). Since the classical IFNγ inducible genes IRF-1 and GBP as well as MHC class I mRNA were not induced by IFNγ in J558 (data not shown), this cell line may have a signaling defect in the IFNγ pathway. Unexpectedly however, and unlike either the MC or Colon 26 cells, TSA induced both CIITA (102-fold) and Iα (537-fold) in J558 as shown in FIGS. 5B and 5D.

Figure 6B:
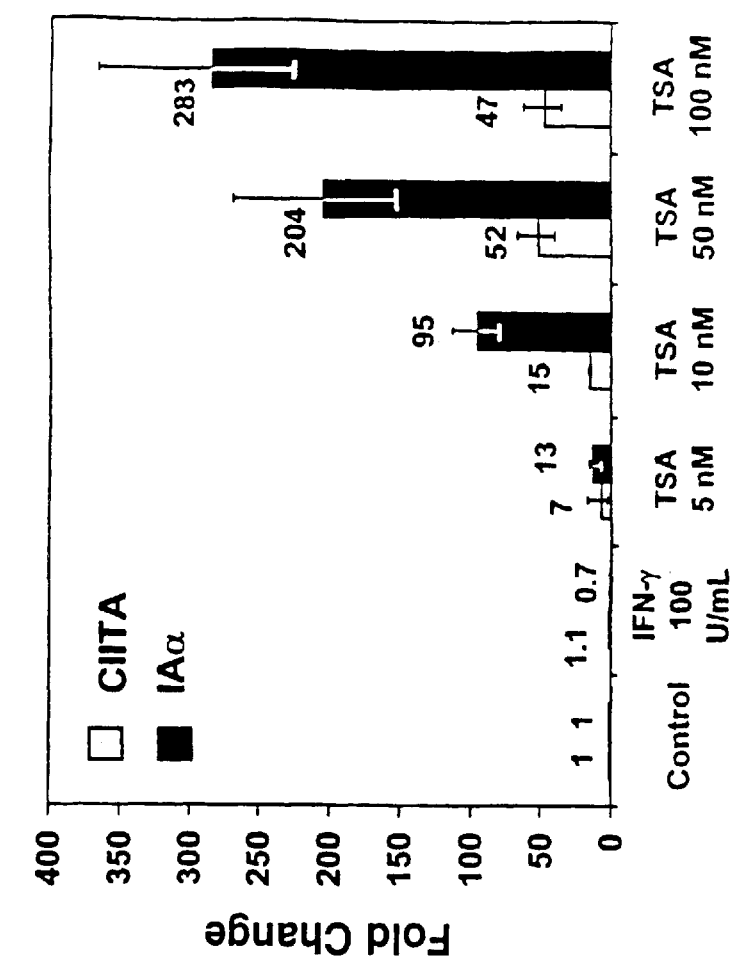
FIGS. 6A and 6B are representations of the effect of IFNγ and various concentrations of the deacetylase inhibitor TSA on mRNA levels of CIITA and IAα in mouse tumor cell line J558.
Figure 6A:
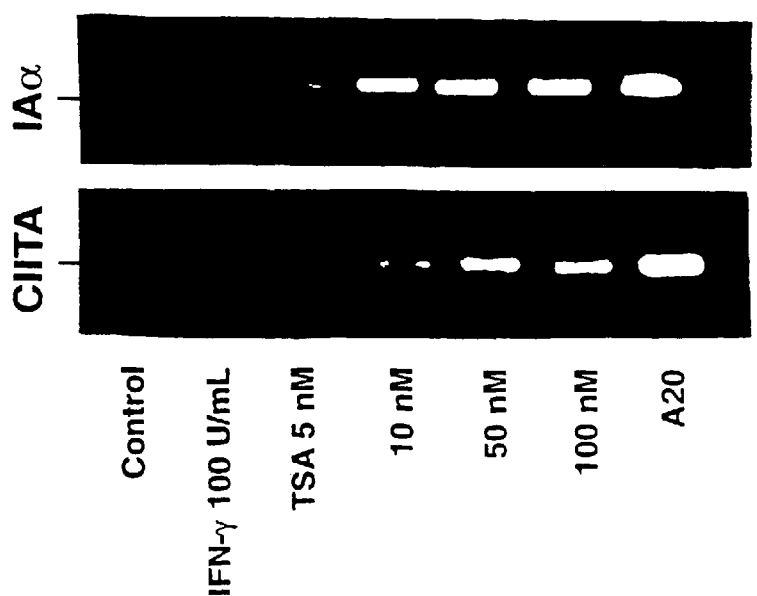

Titration of J558 with TSA was carried out using both RT-PCR (FIG. 6A) and real-time PCR (FIG. 6B). J558 cells were treated with different concentrations of TSA for 12 hours and mRNA was determined by RT-PCR and real-time PCR. Control samples contained small amounts of CIITA and DR, and -fold changes in mRNA levels by real-time are indicated by the numbers over the bars in FIG. 6B. These experiments also clearly demonstrated the distinct effects of TSA and IFNγ. IFNγ failed to activate either CIITA or class II, while TSA induced both CIITA and class II. The contrasting patterns in regard to CIITA induction suggest that TSA may function by both CIITA dependent (in J558) and independent (in MC and Colon 26) mechanisms in different cell types.

EXAMPLE 3

Figure 7B:
Figure 7E:
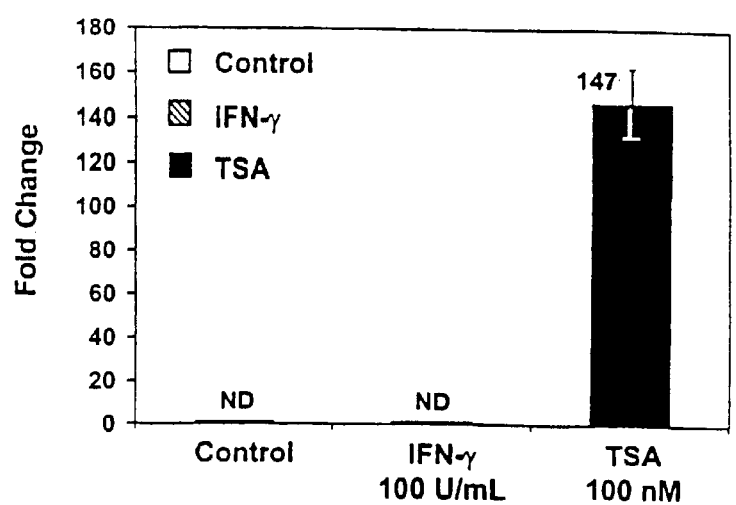
Figure 7C:
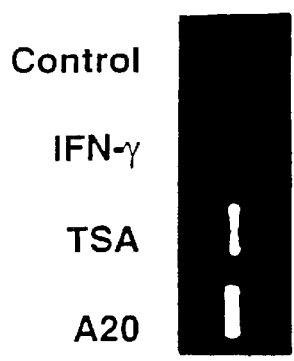
Figure 7F:
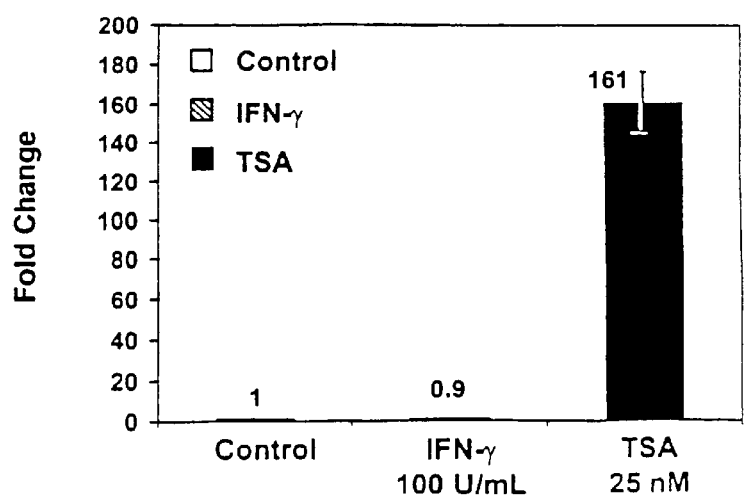

This embodiment illustrates the effect of DAIs on costimulatory molecules. Because of the importance of costimulatory molecules in the cellular activation mechanism involving MHC complexes, the effect of DAIs on the expression of B7-1, B7-2 and CD40 genes was investigated by real-time PCR as well as RT-PCR. While no consistent changes in B7-1 and B7-2 were detected (data not shown), CD40 expression was enhanced by TSA in all three cell types (FIGS. 7A, B, C). MC cells constitutively expressed low levels of CD40 and IFNγ enhanced CD40 mRNA levels 5-fold while TSA elicited a 12-fold increase at 24 hours (FIG. 7A). Colon 26 cells did not constitutively express CD40 and mRNA levels remained undetectable at 60 cycles after 100 U/ml IFNγ treatment for 24 hours. TSA (12 and 48 hours) induced a 147-fold increase in CD40 (FIG. 7B). J558 cells showed low constitutive levels of CD40 mRNA that did not change after treatment with IFNγ while TSA (25 nM for 24 hours) induced a 161-fold increase in CD40. GADPH mRNA remained essentially unchanged with both the primer sites used in RT-PCR and real-time PCR. The lack of induction of CD40 by IFNγ in J558 cells is consistent with the failure of IFNγ to activate other IFNγ inducible genes.

EXAMPLE 4

Figure 8:
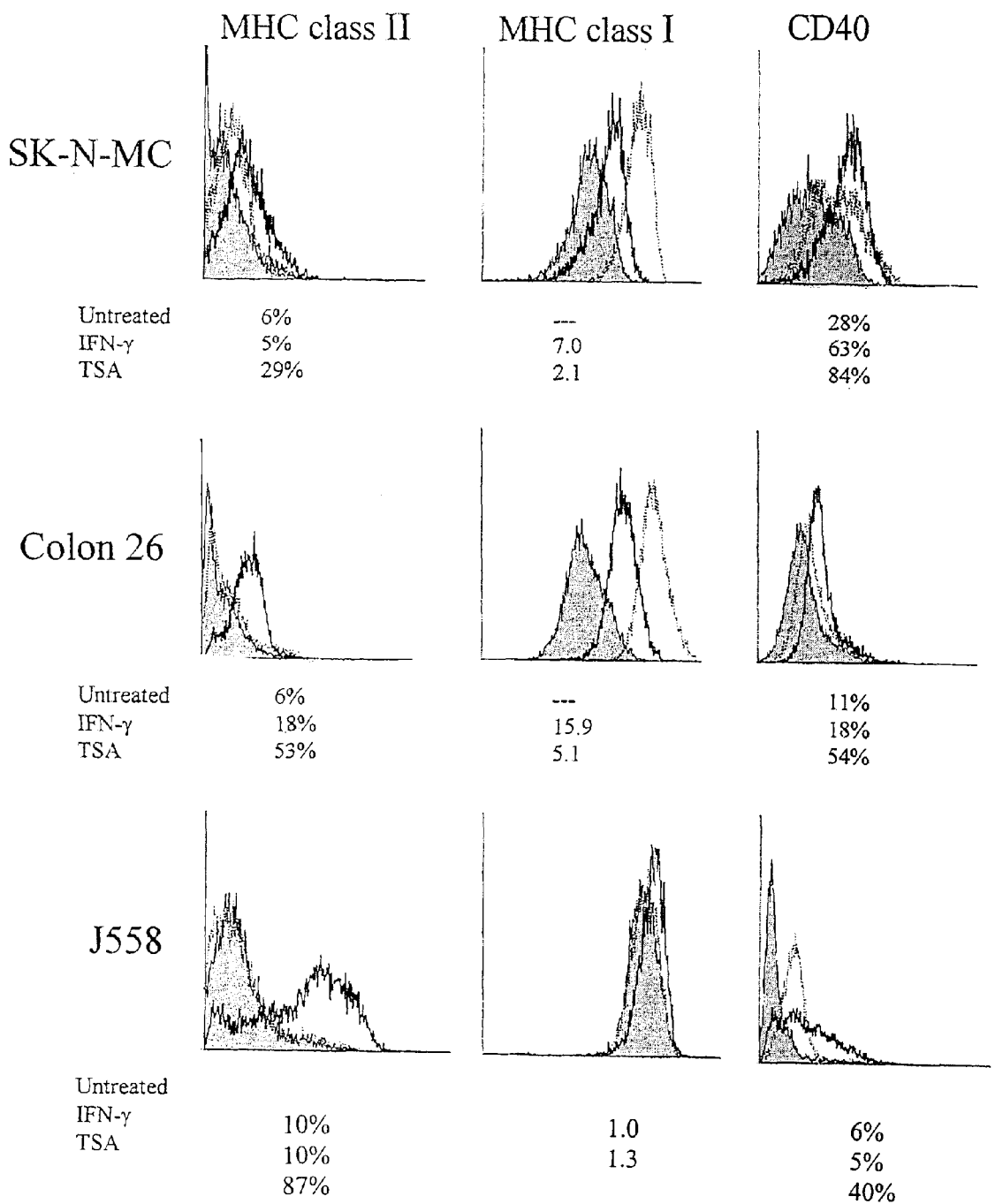
FIG. 8 is a representation of the expression of MHC class I and II and CD40 proteins on the cell surface analyzed by flow cytometry on human neuroblastoma cells SK-N-MC, and mouse tumor Colon 26 and J558 cells.

This embodiment demonstrates that DIAs increase the cell surface protein expression of MHC I, MHC II and CD 40. To determine the effect of TSA on cell surface protein expression, the J558 cell line was subjected to flow cytometric analyses as follows. Flow cytometric analyses were conducted by standard methods using cells fixed with 1.0% paraformaldehyde and analyzed on the FACScan (Becton Dickinson). Cell cycle analyses were carried out by flow cytometry with PI staining of genomic DNA. Cells were fixed and permeablized in methanol, treated with RNaseA and analyzed for DNA content by determination of FL3-area on the FACScan. The FL3-area data were analyzed with the ModFit software for determination of the percent cells in each phase of the cell cycle. In some cases, fluorescein isothiocyanate (FITC)-conjugated antibody staining was conducted prior to PI treatment and surface staining was analyzed as a function of cell cycle phase. Apoptosis was analyzed by staining with annexin-V directly conjugated with either FITC or RPE and by sub-$G_0$ analysis of DNA staining. The results are shown in FIG. 8. Expression levels without treatment are shown as shaded peaks, IFNγ treated cell expression is plotted by a thin line while the level of expression on TSA treated cells is represented by a heavy line. Isotype controls were analyzed and, in each case, fell on or below the levels shown for control cells. MC and Colon 26 treatments are shown for 50 nM TSA for 48 hours, while J558 treatment is for 25 nM TSA for 24 hours. All IFNγ treatments were 100 U/ml for the same length of time as the corresponding TSA treatment. The percent of cells staining positive for MHC class II or CD40 expression is indicated below each histogram. Since all cells were positive for MHC class I expression, the number under the histogram represents -fold change of expression calculated from the mean channel-shift after treatment relative to untreated cells. Data are representative of at least three independent experiments. Of the 13 markers analyzed on J558 cells, only class I, II and CD40 were enhanced, while levels of several non-expressed antigens were not elicited (including CD25, B7 integrin, CD40L, $H2K^k$ and $IA^k$) while other markers, which were expressed, were not altered (including CD44, CD54, CD80, CD86 and CD119) by TSA treatment. In each cell line tested, TSA significantly induced the expression of MHC class II protein on the cell surface (FIG. 8) with induction ranging from 3 to 21-fold, as indicated by mean channel fluorescence, depending on cell line, TSA concentration and length of treatment. The highest expression (21-fold induction) was achieved on J558 cells after 24 hr by 25 nM TSA. IFNγ did not induce class II on any of the cell lines described here. MHC class I expression was also found to be enhanced by TSA in each cell type, but in contrast to the MHC class II, was less effective than IFNγ in MC and Colon 26, while J558 was unresponsive to IFNγ. However, similar to class II data, TSA induced expression of CD40 on all three-cell types and did so more effectively than IFNγ. The separation of control and IFNγ curves in the CD40, J558 experiment depicted in FIG. 8 represents a mean channel fluorescence difference of only 1.3 and was not seen on independent replicates of the experiment.

EXAMPLE 5

This embodiment demonstrates that the concentrations of DIAs useful for the present invention produce little or no apoptosis or that the effect seen in the present invention is not likely to be due to the effect of DAIs on cell cycle. TSA has been described as a cell cycle inhibitor that induces both $G_1$ and especially $G_2/M$ blocks (Bestor, 1998, *Nature,* 393:311–312; Yoshida et al., 1988, *Exp. Cell Res.* 177:122–131). MHC class II, but not class I, has been reported (Inokoshi et al., 1999, *Biochem. Biophys. Res. Commun.,* 256:372–376; Monroe et al., 1983, *J. Immunol.,* 130:626–631) to be regulated differentially during the cell cycle. Therefore the cell cycle of the cell lines used in the present invention was analyzed by DNA staining and flow cytometry with each of the treatment conditions under study. Since it was observed that some TSA concentrations significantly altered the cell cycle, experiments were designed to include conditions that did not affect cell cycle progression in the cell lines examined. The results (data not shown) indicated that the concentrations used in FIG. 8 did not significantly alter the cell cycle, and yet 29% of cells were positive for class II expression in MC, 53% in Colon 26 and 87% in J558. Two additional methods were used to analyze cell cycle effects on MHC expression. Since it has been reported that TSA arrests cell cycle mainly in $G_2/M$, and class II has been reported to accumulate in $G_2/M$ (Monroe et al., 1983, supra), experiments were designed to essentially arrest 100% of J558 cells in $G_2/M$ with nocodazole. Nocodazole treatment resulted in 23% MHC class II positive cells while TSA produced 75% positive cells (data not shown). Further, using double staining with PI and antibody to class I on J558 cells, it was observed that TSA induced expression throughout the cell cycle and enhancement was not restricted to a specific phase. From the above experiments, it can be concluded that DAIs have specific effects on MHC class I and II, and CD40 gene expression, which is likely not a result of its action on the cell cycle.

TSA has been reported by others (Yoshida et al., 1988, supra), to induces apoptosis. In order to evaluate a potential role for apoptosis in the altered gene expression by TSA, apoptosis by flow cytometry through DNA staining with PI (the "sub-$G_0$" population), and staining with annexin-V was monitored. At the low concentrations of TSA employed in the experiments represented in FIG. 8, selected for a normal cell cycle, apoptosis could not be detected. Thus, it can be concluded that deacetylase inhibitors have specific effects on MHC class I and class II, and CD40 gene expression that are likely not a result of apoptosis.

It should be understood that the examples disclosed herein are for illustrative purposes only and other modifications of the embodiments of the present invention that are obvious to those skilled in the art are intended to be within the scope of the present invention.

What is claimed is:

1. A method for increasing the expression of CD40 gene in tumor cells in vitro comprising the step of contacting the tumor cells with an effective amount of a deacetylase inhibitor wherein said amount of deacetylase inhibitor increases the expression of CD40 on said cells.

2. The method of claim 1, wherein the deacetylase inhibitor is trichostatin A.

3. The method of claim 1, wherein the deacetylase inhibitor is sodium butyrate.

* * * * *

UNITED STATES PATENT AND TRADEMARK OFFICE
CERTIFICATE OF CORRECTION

PATENT NO. : 6,518,012 B1
DATED : February 11, 2003
INVENTOR(S) : Tomasi

It is certified that error appears in the above-identified patent and that said Letters Patent is hereby corrected as shown below:

Column 1,
Line 13, first paragraph, please insert
-- This invention was made with Government support under Grant
No. R01 HD17013 awarded by the National Institutes of Health.
The Government has certain rights in the invention. --

Signed and Sealed this

Twenty-ninth Day of April, 2003

JAMES E. ROGAN
*Director of the United States Patent and Trademark Office*